United States Patent

Gustafsson et al.

Patent Number: 5,728,082
Date of Patent: Mar. 17, 1998

[54] ABSORBENT BODY WITH TWO DIFFERENT SUPERABSORBENTS

[75] Inventors: Lars Gustafsson, Göteborg; Stefan Areskoug, Mölnlycke; Magnus Qvist, Floda, all of Sweden

[73] Assignee: Molnlycke AB, Goteberg, Sweden

[21] Appl. No.: 345,423

[22] Filed: Nov. 19, 1994

Related U.S. Application Data

[63] Continuation of Ser. No. 261,302, Jun. 16, 1994, abandoned, which is a continuation of Ser. No. 916,842, filed as PCT/SE91/00101, Feb. 13, 1991 published as WO91/11978, Aug. 22, 1991, abandoned.

[30] Foreign Application Priority Data

Feb. 14, 1990 [SE] Sweden ............... 90005349

[51] Int. Cl.$^6$ .................. A61F 13/15; D04H 1/08; B32B 5/16

[52] U.S. Cl. ................. 604/368; 428/281; 428/283; 604/378

[58] Field of Search ................ 604/358, 365–368, 604/383, 378; 428/288–290, 283–284, 286–287, 281

[56] References Cited

U.S. PATENT DOCUMENTS

| | | | |
|---|---|---|---|
| Re. 32,649 | 4/1988 | Brandt et al. | 604/368 |
| 3,425,971 | 2/1969 | Gugliemelli et al. | 266/17.4 |
| 3,661,815 | 5/1972 | Smith | 260/17.4 |
| 3,935,099 | 1/1976 | Weaver et al. | 210/43 |
| 4,251,643 | 2/1981 | Harada et al. | 525/57 |
| 4,338,371 | 7/1982 | Dawn et al. | 604/368 |
| 4,578,068 | 3/1986 | Kramer et al. | 604/368 |
| 4,605,402 | 8/1986 | Iskra | 604/368 |
| 4,673,402 | 6/1987 | Weisman et al. | 604/368 |
| 4,699,823 | 10/1987 | Kellenberger et al. | 604/368 |
| 5,147,343 | 9/1992 | Kellenberger | 604/372 |

FOREIGN PATENT DOCUMENTS

| | | |
|---|---|---|
| 254476 | 1/1988 | European Pat. Off. |
| 401189 | 12/1990 | European Pat. Off. |
| 463747 | 1/1991 | Sweden |
| 2048078 | 12/1980 | United Kingdom |
| 2145661 | 4/1985 | United Kingdom |

OTHER PUBLICATIONS

Lecture given at a conference IIMPACT 87 Feb. 26–27, 1987 (copies of pages Section IX–1–6 and 8–9).

*Primary Examiner*—John G. Weiss
*Assistant Examiner*—K. M. Reichle
*Attorney, Agent, or Firm*—Burns, Doane, Swecker & Mathis, LLP

[57] ABSTRACT

The invention relates to an absorbent body for use in diapers or like articles. The invention is characterized in that the absorbent body includes a first layer of fluff, a first superabsorbent mixed in the fluff layer and having a high degree of cross-linking, and in that the absorbent body includes a second layer which contains a second superabsorbent having a higher liquid absorbency than the first superabsorbent.

7 Claims, 2 Drawing Sheets

ABSORBENT BODY WITH TWO DIFFERENT SUPERABSORBENTS

This application is a continuation of application Ser. No. 08/261,302, filed Jun. 16, 1994, which application is a continuation of application Ser. No. 07/916,842, filed as PCT/SE91/00101, Feb. 13, 1991, published as WO91/11978, Aug. 22, 1991, now both abandoned.

BACKGROUND OF THE INVENTION

1. Field of the Invention

The present invention relates to an absorbent body or pad for use in diapers, incontinence guards or like articles.

2. Description of Related Art

It is highly essential that the absorbent pad of a diaper has a high absorption rate. The absorbent pad will normally exhibit a high absorption rate when dry, since the pulp core will then enclose a sufficient quantity of air which can be displaced rapidly and replaced with urine.

The fibres of the fluff mat in a dry absorbent pad are relatively rigid and are therewith able to withstand a certain amount of weight before becoming compressed. The fibres lose much of their ability to withstand weight or pressure when the pad is wet, therewith causing the fluff mat to collapse.

A large part of the pad volume is lost when the fluff mat has collapsed. The ability of the fluff mat to further absorb liquid is then restricted to the ability of the fluff to transport the urine from one location to another. The majority of fluffs manage this with differing degrees of success, but the process of transportation is very slow within the fluff mat and the transportation of excess urine is a constant concern. This excess is the difference between the amount of liquid present in the fluff at a particular moment and the ability of the fluff to retain liquid.

As mentioned, superabsorbents are able to absorb large quantities of urine, about 3–5 times the absorbency of fluff. Although this ability can be utilized, it is not particularly effective when solely one absorption ability is exchanged for the other. Superabsorbents can also contribute to other properties, such as improved surface dryness, etc., for instance.

The greatest obstacle to rapid, secondary absorption in a fluff mat which has collapsed at the first absorption, is that there is no air in the wet fluff to displace.

SUMMARY

The present invention provides a solution to this problem.

The inventive absorbent pad is characterized in that the pad includes a first layer of fluff which, when the article is in use, lies nearest the wearer, a first super absorbent which is disposed in said fluff layer and which has a high degree of cross-linking and therewith the ability to swell while being substantially unaffected by normally occurring pressures, whereby subsequent to liquid absorption the collapsed pulp is loosened and again forms an air-containing voluminous fluff layer, and in that the absorbent pad includes a second layer in which there is disposed a second superabsorbent whose liquid absorbing capacity is greater than that of the first superabsorbent.

It has been found that a superabsorbent having a very high degree of cross-linking, with subsequent high gel strength, is able to loosen the wet fluff while emptying the fluff of liquid at the same time. It will be understood that the total absorbency of the absorbent pad is not solely dependent on how much liquid the fluff and the superabsorbent can absorb individually.

The total absorbency is greatly dependent on the size of the volume that can be retained under the pressure forces that occur.

According to the invention, a highly cross-linked superabsorbent shall improve the rate at which a subsequent liquid discharge is absorbed, by loosening or "fluffing" the collapsed fluff mat and increasing the total volume of the wet region.

A superabsorbent which is so highly cross-linked that it can swell while being substantially unaffected by normally occurring pressures has a lower absorbency than a superabsorbent which has a lower degree of cross-linking. Consequently, the inventive absorbent pad includes a second layer which incorporates a second superabsorbent having a higher liquid absorbing capacity.

BRIEF DESCRIPTION OF THE DRAWINGS

The invention will now be described in more detail with reference to the accompanying drawings.

DETAILED DESCRIPTION OF PREFERRED EMBODIMENTS

Figure 1:
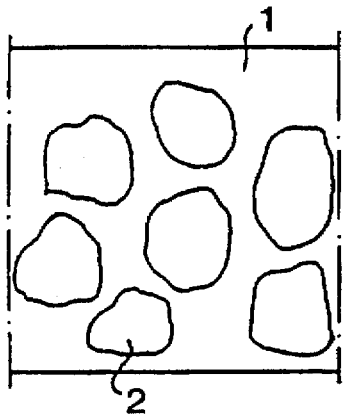
FIGS. 1 and 2 illustrate schematically the state of a crosslinked superabsorbent contained in a fluff mat, both before and after liquid absorption, respectively.
Figure 2:
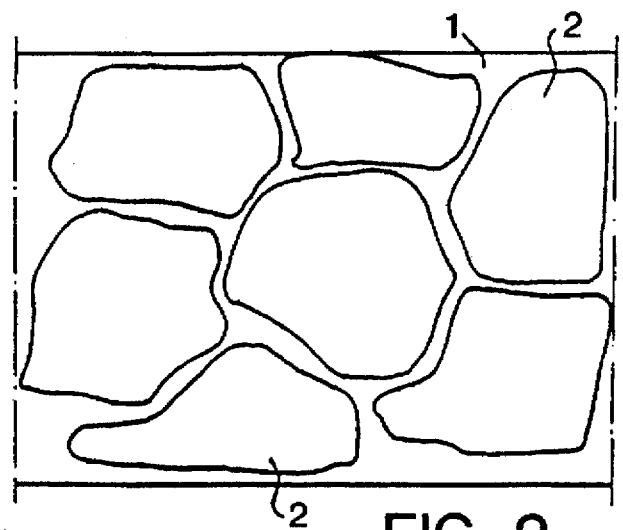

FIG. 1 illustrates a fluff layer 1 in which grains or particles of cross-linked superabsorbent 2 are mixed. The fluff mat illustrated in FIG. 1 is in a dry, voluminous state with an abundancy of air between the fibres. The absorbent pad shown in FIG. 1 can therefore rapidly absorb liquid penetrating into the pad. When the fluff mat becomes wet, it collapses under the weight of absorbed liquid and under the pressure exerted by external loads and if no superabsorbents were present the collapsed fluff mat would discharge liquid when the absorbent pad is subjected to further, external pressures. The superabsorbents 2 present in the fluff mat 1 take liquid from the fluff by suction and increase in size, by swelling. The superabsorbents 2 are cross-linked to an extent such as to possess sufficient gel strength to retain absorbed liquid under normal pressure in use, i.e. normal pressures on the absorbent pad of a diaper. As illustrated in FIG. 2, the superabsorbents 2 do not form a continuous gel, but remain in the form of mutually separate grains or particles, even in their swollen state. As before-mentioned, the superabsorbents are also able to retain liquid when subjected to normal pressures in use, but do not retain their shape and are liable to be flattened laterally when subjected to pressure. The superabsorbents 2 are therefore not able to loosen the fluff, and the fluff mat will therefore remain substantially in a collapsed state. The absorbent pad shown in FIG. 2 is therefore not able to quickly absorb further liquid.

Diaper manufacturers now desire superabsorbents whose gel strength will enable absorbed liquid to be retained effectively in the swollen gel even when subjected to pressure. The liquid absorbency of a superabsorbent decreases, however, with increased degrees of cross-linking and therewith increased gel strength.

At present there is no superabsorbent which has a sufficiently high liquid absorbency while being capable, at the same time, of loosening up a collapsed fluff mat.

Figure 3:
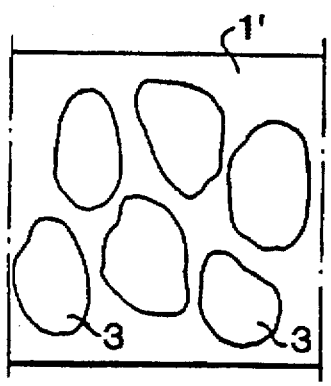
FIGS. 3 and 4 illustrate schematically the state of a highly cross linked superabsorbent contained in a fluff mat, both before and after liquid absorption, respectively.
Figure 4:
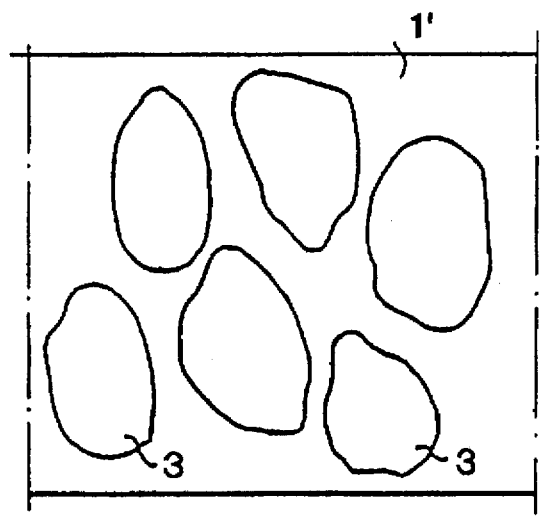

FIG. 3 illustrates a fluff mat 1' in which there are mixed superabsorbents 3 which have a high degree of cross-linking and therewith a high gel strength. As will be understood, the fluff mat 1' shown in FIG. 3 will collapse in the same way as that described with reference to FIG. 1 when the mat absorbs liquid. The superabsorbents 3, however, are so highly cross-linked and of such a high gel strength that they are able to swell under normal use pressure in a diaper or the like, without changing shape. Consequently, when the superabsorbent particles 3 swell, the fluff mat 1' will be loosened or "fluffed", as illustrated in FIG. 4. The fluff mat is emptied of liquid, at the same time as it is loosened by the superabsorbent. Subsequent to swelling of the superabsorbent and loosening of the fluff mat, the absorbent pad illustrated in FIG. 4 will contain a large amount of air which can be readily displaced when further liquid is absorbed.

Figure 5:
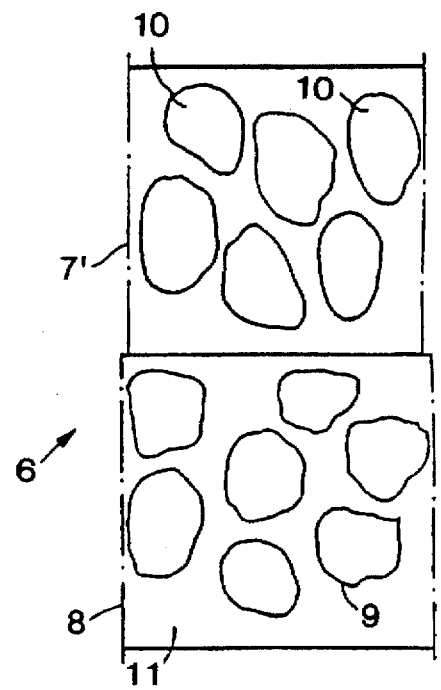
FIG. 5 illustrates an absorbent body according to the present invention having two layers together.

An inventive absorbent pad 6 (FIG. 5) is constructed from an upper layer 7 of the kind described with reference to FIGS. 3 and 4, this layer laying nearest the user when the absorbent pad is used in a diaper, and a bottom layer 8 which includes a superabsorbent 9 whose liquid absorbency is greater than the absorbency of the superabsorbent 10 of the upper layer.

The bottom layer of the inventive absorbent pad may, for instance, be constructed in the manner described with reference to FIGS. 1 and 2 i.e., superabsorbent 9 is mixed in a fluff 1.

The superabsorbent 9 in the bottom layer 8 may optionally comprise a superabsorbent having a gel strength which is so low as to form a continuous gel. The important criterion in this respect is that the upper layer is able to repeatedly absorb liquid quickly.

One example of a gel which exhibits a very high gel strength and which functions effectively in the upper layer of the inventive absorbent pad is "SALSORB" DPX5038.

Good results have been achieved with "AQUALIC" CA W-2 in an upper fluff layer and while using the similarly cross-linked superabsorbent "AQUALIC" CA W-4 in the bottom layer. According to the manufacturer, "AQUALIC" CA W-2 has a higher degree of cross-linking and therewith greater gel strength than "AQUALIC" CA W-4.

All of the superabsorbents mentioned by way of example are cross-linked sodium polyacrylates.

It will be understood that the invention is not limited to the aforedescribed embodiment and that several modifications can be made within the scope of the following claims.

Figure 6:
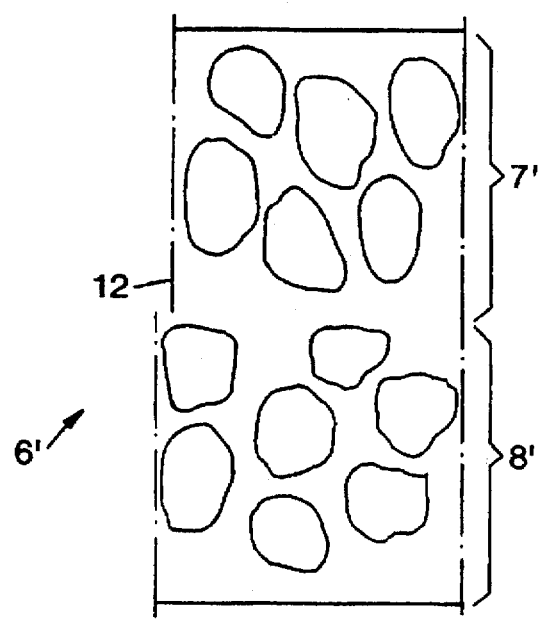
FIG. 6 illustrates an absorbent pad having an integrally configured fluff body which incorporates different layers of different superabsorbents.

For instance (FIG. 6), an inventive absorbent pad 6' may comprise an integrally configured fluff body 12 which incorporates different layers 7', 8' of different superabsorbents 9', 10'.

We claim:

1. An absorbent body for use in an absorbent article to be worn by a wearer, comprising:

an air containing voluminous first layer of fluff which lies nearest the wearer in use, a first superabsorbent mixed in said first layer and which has a degree of cross-linking providing a gel strength high enough so as to swell under normal use pressure in said article without changing shape so that the fluff of the first layer, which collapses when absorbing liquid, will be loosened and therewith again form an air-containing, voluminous layer of fluff, and a second layer containing a second superabsorbent wherein said second superabsorbent has a higher liquid absorbency, when in use by a wearer, than the first superabsorbent and thus absorbs more liquid than the first superabsorbent.

2. An absorbent body according to claim 1, wherein the second layer comprises fluff in which the second superabsorbent is mixed.

3. An absorbent body according to claim 1, wherein the second superabsorbent in said second layer is cross-linked but has a lower gel strength than the first superabsorbent.

4. An absorbent body according to claim 2, wherein the second superabsorbent in said second layer is cross-linked but has a lower gel strength than the first superabsorbent.

5. An absorbent body according to claim 1, wherein the second superabsorbent has a lower gel strength than the first absorbent means and is sufficiently low to form a continuous gel.

6. An absorbent body, comprising:

a first layer of fluff;

first superabsorbent means for swelling to a new size that is proportional to an original shape thereof in said first layer, said first superabsorbent means having a gel strength to enable it to swell under normal use pressure;

a second layer of fluff;

second superabsorbent means for absorbing a liquid in said second layer, said second superabsorbent means having a liquid absorbency greater than a liquid absorbency of said first superabsorbent means, when in use by a wearer, so that the second superabsorbent means absorbs more liquid than the first superabsorbent means.

7. An absorbent body according to claim 6, wherein the second superabsorbent means has a lower gel strength than the first absorbent means and is sufficiently low to form a continuous gel.

* * * * *